(12) United States Patent
Deininger et al.

(10) Patent No.: US 7,537,474 B2
(45) Date of Patent: May 26, 2009

(54) LEAD RECEPTACLE AND PIN FRAME ASSEMBLY

(75) Inventors: Steve T. Deininger, Blaine, MN (US); Jeffrey J. Clayton, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/776,733

(22) Filed: Jul. 12, 2007

(65) Prior Publication Data

US 2009/0017668 A1 Jan. 15, 2009

(51) Int. Cl.
*H01R 27/00* (2006.01)
(52) U.S. Cl. .................................. 439/218
(58) Field of Classification Search .............. 439/218, 439/346, 222, 82, 140, 583, 651, 814
See application file for complete search history.

(56) References Cited

U.S. PATENT DOCUMENTS

| 5,007,864 | A | * | 4/1991 | Stutz, Jr. ................ 439/651 |
| 5,951,595 | A | * | 9/1999 | Moberg et al. ............ 607/37 |
| 6,115,634 | A | | 9/2000 | Donders |
| 6,574,508 | B2 | | 6/2003 | Zaouali |
| 6,854,994 | B2 | * | 2/2005 | Stein et al. ............... 439/218 |
| 2003/0050549 | A1 | | 3/2003 | Sochor |
| 2003/0163171 | A1 | | 8/2003 | Kast |
| 2004/0116976 | A1 | | 6/2004 | Spadgenske |
| 2005/0065570 | A1 | * | 3/2005 | Stein et al. ............... 607/37 |
| 2007/0087637 | A1 | | 4/2007 | Zart |

FOREIGN PATENT DOCUMENTS

| WO | WO 98/48896 | 11/1998 |
| WO | WO 03/034892 | 5/2003 |

OTHER PUBLICATIONS

PCT Search Report dated Aug. 21, 2008.

* cited by examiner

*Primary Examiner*—Jean F Duverne
(74) *Attorney, Agent, or Firm*—Campbell Nelson Whipps LLC

(57) ABSTRACT

A method includes (i) placing about a first alignment pin a first lead receptacle having a conductive portion, and (ii) placing about a second alignment pin a second lead receptacle having a conductive portion. The method further includes placing the first and second lead receptacles on a restraining fixture and attaching and electrically coupling a first conductor of a one piece lead frame pin assembly to the conductive portion of the first receptacle. The lead frame pin assembly has a tab element connecting the first conductor to a second conductor. The first and second conductors each include a feedthrough coupling portion. The method also includes attaching and electrically coupling the second conductor of the lead frame assembly to the conductive portion of the second receptacle. The lead receptacle and pin assembly may be inserted into a connector header.

16 Claims, 12 Drawing Sheets

LEAD RECEPTACLE AND PIN FRAME ASSEMBLY

FIELD

This disclosure relates, inter alia, to implantable medical devices. More particularly, it relates to lead receptacles that operably couple medical leads to medical devices.

BACKGROUND

Many implantable medical devices, such as neurostimulators, pacemakers and defibrillators, transmit electrical signals to provide therapy to a patient. Electrical signals generated by the devices may be delivered to the patient tissue via electrodes disposed at a distal portion of a medical lead. The lead is electrically coupled to the device via a connector block or header of the device. The connector header includes a receptacle into which a lead may be inserted.

Typically, pins, which are electrically coupled to electronics of the device, are fed through a hermetically sealed housing of the device. The receptacle of the connector header contains conductive elements that are electrically coupled to the pins. The lead is insertable into the receptacle such that electrical contacts of the lead may be electrically coupled to the conductive elements of the receptacle. Conductors electrically couple the contacts of the lead to the electrodes.

Typical connector headers include a polyurethane housing and are made generally as follows. The lead receptacles are placed into the molded polyurethane housing or, alternatively, are placed into a polysulfone or other rigid polymeric frame over which the polyurethane housing is placed. Adhesive is used to bond the receptacles to the housing, the conductive elements of the receptacles are welded to the feedthrough pins, the housing is then filled with liquid silicone rubber or other suitable overmold or adhesive polymer, and the connector header housing is then secured to the housing of the device. As the lead receptacles are typically held together by a longitudinally compressive force, placement of the receptacles into the frame can be challenging. In addition, welding the conductive elements to the receptacle while in the frame can result in misalignment of the receptacle.

SUMMARY

The present disclosure describes, inter alia, systems, devices, and methods that employ a one-piece receptacle and conductor pin frame assembly having a more rigid, more dimensionally stable configuration.

In an embodiment, a method of manufacture is described. The method includes (i) placing about a first alignment pin a first lead receptacle having a conductive portion, and (ii) placing about a second alignment pin a second lead receptacle having a conductive portion. The method further includes placing the first and second lead receptacles on a restraining fixture and attaching and electrically coupling a first conductor of a one piece lead frame pin assembly to the conductive portion of the first receptacle. The lead frame pin assembly has a tab element connecting the first conductor to a second conductor. The first and second conductors each include a feedthrough coupling portion. The method also includes attaching and electrically coupling the second conductor of the lead frame assembly to the conductive portion of the second receptacle. The lead receptacle and pin assembly may be inserted into a connector header.

In an embodiment, a lead receptacle and pin assembly is described. The lead receptacle and pin assembly includes (i) first and second lead receptacles, each having a conductive portion, and (ii) a one-piece lead frame pin assembly having first and second conductors. The first and second conductors are connected via a tab element. The first conductor is attached and electrically coupled to the conductive portion of the first lead receptacle, and the second conductor is attached and electrically coupled to the conductive portion of the second lead receptacle.

By providing devices, systems and methods employing a one-piece receptacle and conductor pin frame assembly having a more rigid, dimensionally stable configuration, insertion of receptacles into a header housing is facilitated and alignment of the receptacle following placement is enhanced. These and other advantages will be readily understood from the following detailed descriptions when read in conjunction with the accompanying drawings.

Figure 1:
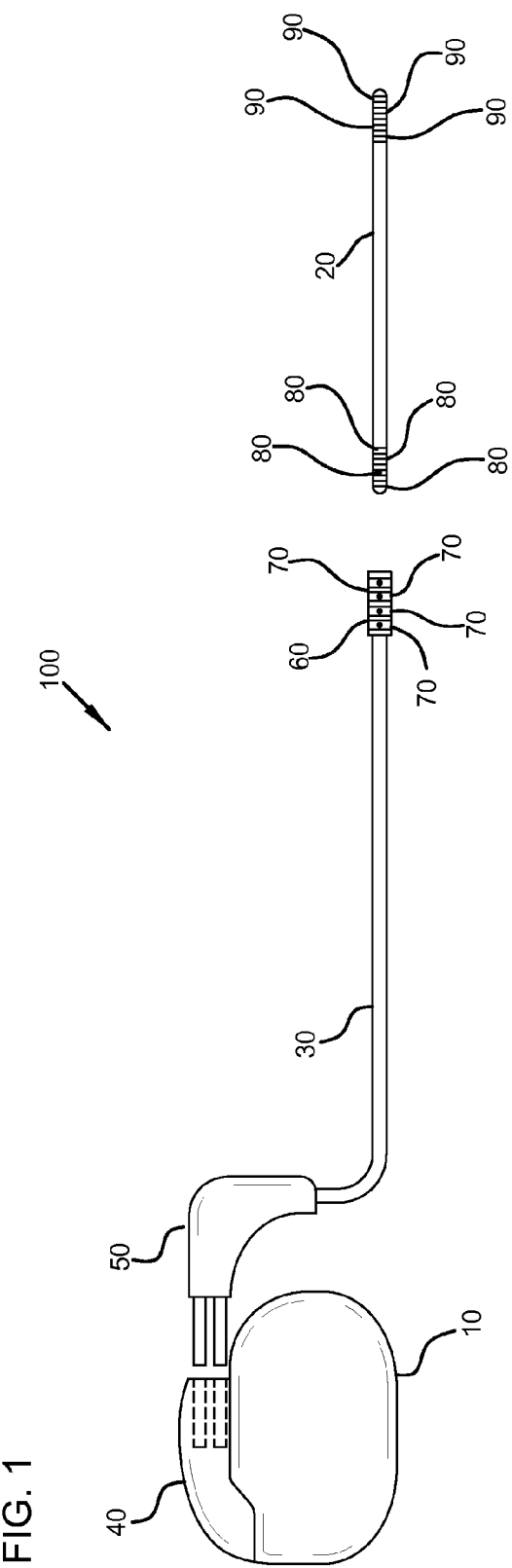
FIG. 1 is a diagrammatic representation of an exploded view of a representative neurostimulation system.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices, and methods that employ a one-piece receptacle and conductor pin frame assembly having a more rigid, more dimensionally stable configuration. The use of such assemblies can reduce manufacturing time due to the ease of insertion into, e.g., connector headers for implantable medical devices. In addition, tighter dimensional tolerances of the receptacles and resultant connection headers are achievable. For example, lead insertion force into connector headers having receptacles manufactured according to the principles described herein have been found to be substantially reduced.

The teachings presented herein are applicable to any implantable medical device system employing a device having electronics, an apparatus for carrying electrical signals from the electronics to the patient, from the patient to the electronics, or the like, and a lead receptacle for operably coupling the apparatus to the device. For example, the apparatus may include a sensor for providing signals to the electronics or may include an electrode for delivering electrical signal to the patient. For the sake of convenience, the device may often be described as an implantable electrical signal generator but it will be understood that the device may be any suitable device, including, for example, a monitoring device.

Referring to FIG. 1, an exploded view of an embodiment of a representative system 100 is shown. The system 100 includes an implantable electrical signal generator 10, a lead extension 30 and a lead 20. Implantable electrical signal generator 10 includes a connector header 40 configured to receive plug 50 at proximal end of lead extension 30 or other adaptor to couple lead 20 to electrical signal generator 10. The distal end portion of lead extension 30 includes a connector 60 configured to receive proximal end portion of lead 20. Connector 60 includes internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). In general, a lead 20 may include any number of electrodes 90, e.g. one, two, three, four, five, six, seven, eight, or sixteen. Typically, each electrode 90 is electrically coupled to a discrete electrical contact 80. While not shown, it will be understood that more than one lead 20 may be operably coupled to one electrical signal generator 10 or one extension 30 or that more than one extension 30 may be operably coupled to one electrical signal generator 10. It will be further understood that lead 20 may be coupled to electrical signal generator 10 without use of extension 30 or adaptor.

Figure 2A:
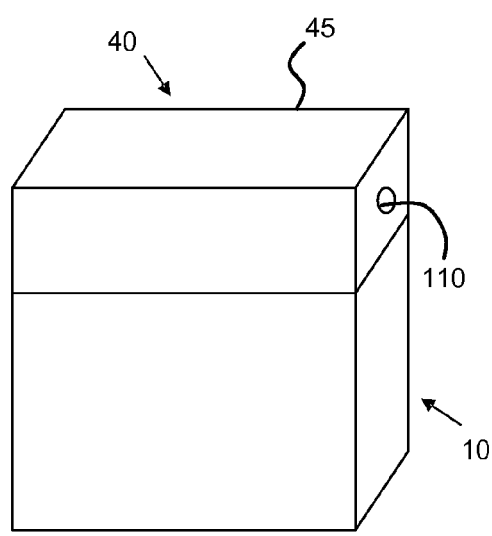
FIGS. 2A-D are schematic drawings of perspective views of representative devices with associated connection headers.
Figure 2B:
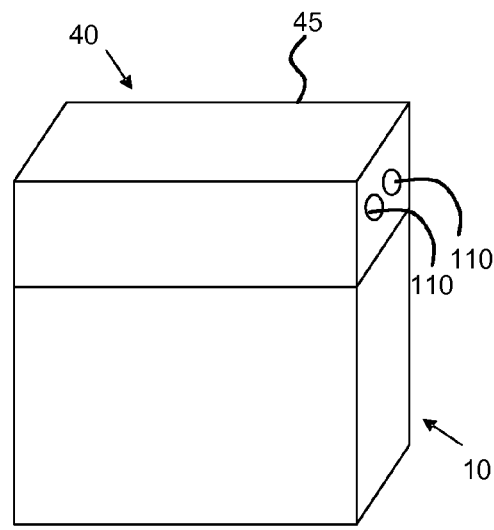
Figure 2C:
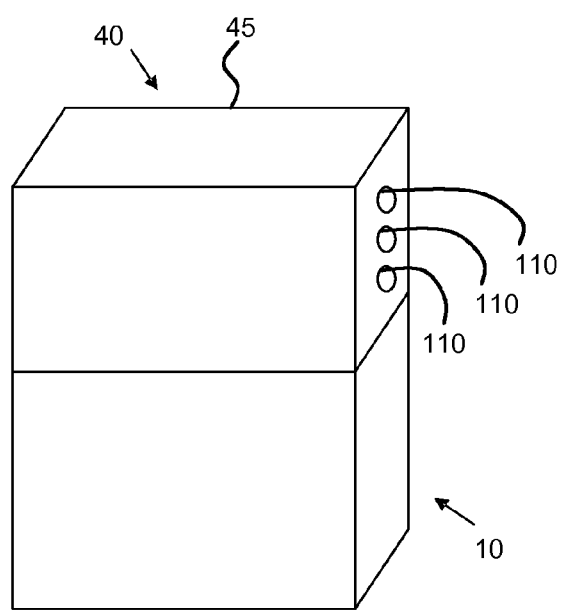

As shown in the embodiments depicted in FIGS. 2A-C, connector header 40 may include any number of openings 110 defined by header housing 45 for receiving lead, lead extension, adaptor, or the like. Openings 110 may be arranged in any suitable orientation with respect to connector header 40 or device 10.

Figure 2D:
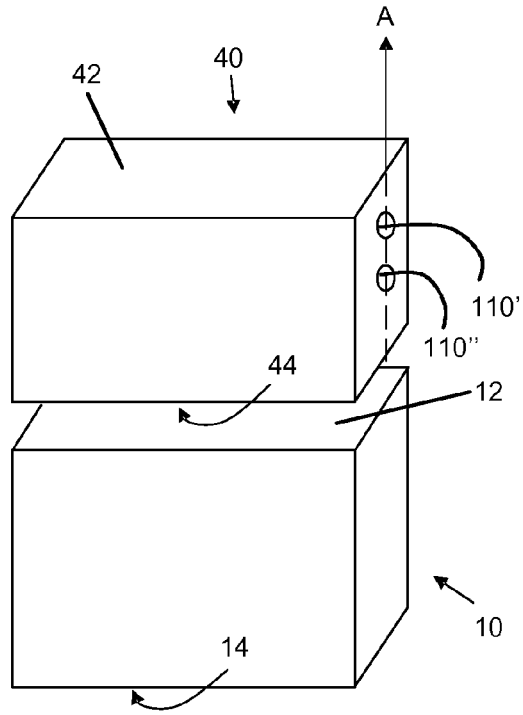

Referring to the view in FIG. 2D in which header 40 is removed from device 10, device 40 has a top 12 and bottom 14 surface and header 40 has a top 42 and bottom 44 surface. At least a portion of bottom surface 44 of header 40 is disposed on at least a portion of top surface 12 of device 10 when header 40 is connected to device 10. A longitudinal axis A runs through header 40 from bottom to top. In various embodiments, header 45 has a first opening 110' configured to receive a lead (not shown in FIG. 2D) and a second opening 110" configured to receive a lead and disposed between the first opening 110' and the bottom surface 44 of the header 40. In some embodiments, first and second openings 110', 110" are substantially parallel to the longitudinal axis A.

Figure 3:
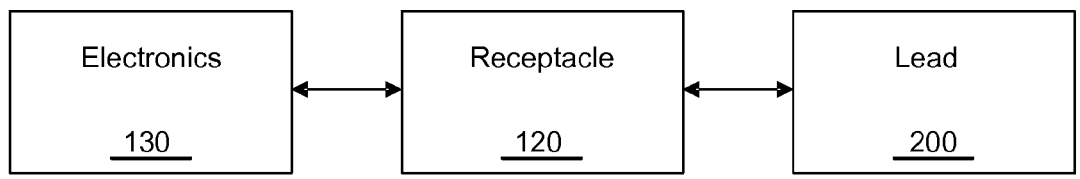
FIG. 3 is a block diagram of a system showing a connector header receptacle operably coupling electronics of a device to a lead.

Referring to FIG. 3, a block diagram of a representative system is shown. Generally, receptacle 120 operably couples a lead 200 to electronics 130 of implantable device. For the sake of convenience, lead 200 will be used hereinafter to refer to lead 20, lead extension 30, or adaptor configured to couple lead 20 or extension 30 to receptacle 120 in connector header 40, as well as any apparatus that may be used to carry an electrical signal to or from device 10.

Figure 4:
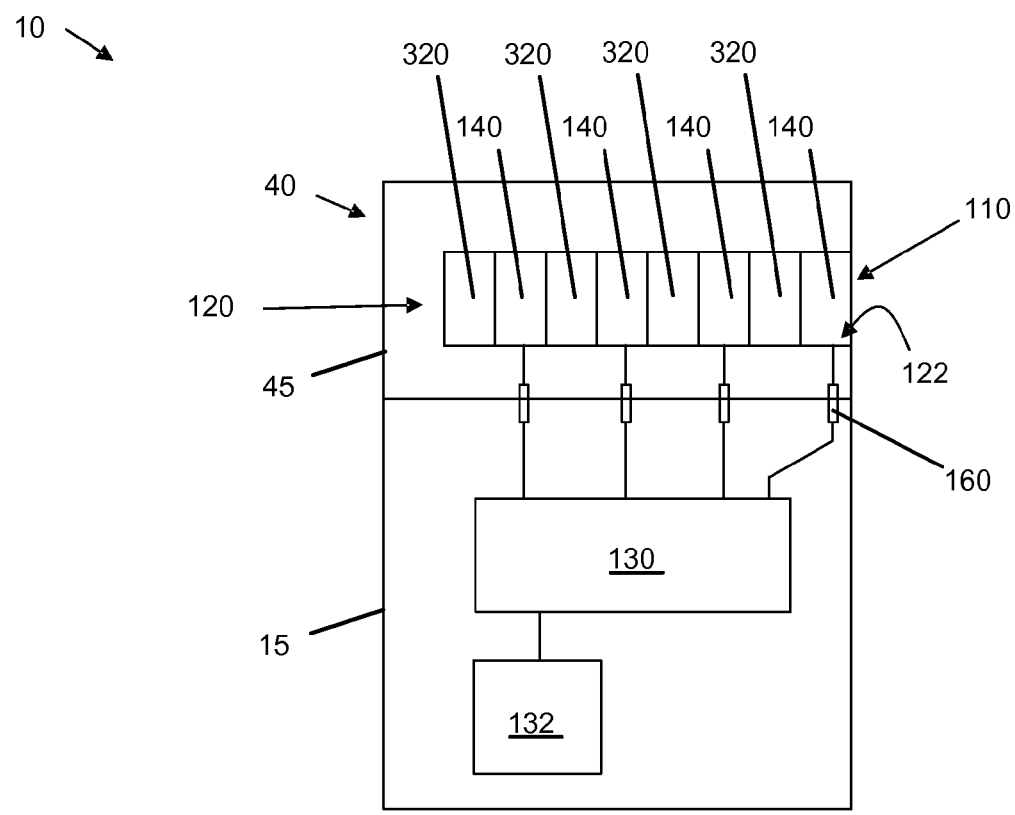
FIGS. 4, and 5A-B are schematic cross sections showing portions of devices and connector headers.
Figure 5A:
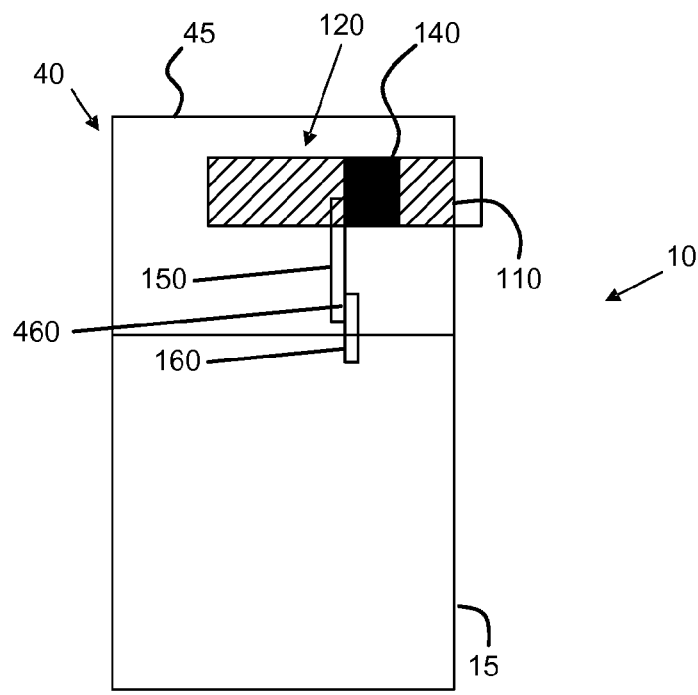

FIGS. 4-5 are a schematic diagram cross section view showing some components of a representative implantable medical devices 10. Device 10 has a hermetically sealed housing 15 defining a sealed housing interior. A power source 132 and electronics 130 are disposed within the housing interior. The power source 132 is operably coupled to the electronics 130. Hermetic feedthrough assemblies 160 having conductors protruding from the exterior of device housing 15 are electrically coupled to electronics 130. The device 10 further includes a connector header 40 having a housing 45 connected to the device housing 15. A lead receptacle 120, which in many embodiments is generally cylindrical, projects into header housing 45 and has an inner surface 122 defining an aperture configured to receive a lead. The lead receptacle aperture is axially aligned with and in communication with an opening 110 defined by header housing 45. Lead receptacle 120 includes alternating conductive 140 and non-conductive 320 elements. Conductive elements 140 are positioned in header 40 such that an electrical contact of a lead may be electrically coupled to a conductive element 140 when the lead is inserted into the receptacle 120. Conductive elements 140 are electrically coupled to conductors of the feedthroughs 160, via feedthrough conductive portion 460 of conductor 150 as shown in, e.g., FIG. 5A. Conductors 150 may be made of any suitable material, such as platinum, platinum iridium, titanium, tantalum, nickel-cobalt-molybdenum alloys, and the like and may be molded, stamped or otherwise formed.

Figure 5B:
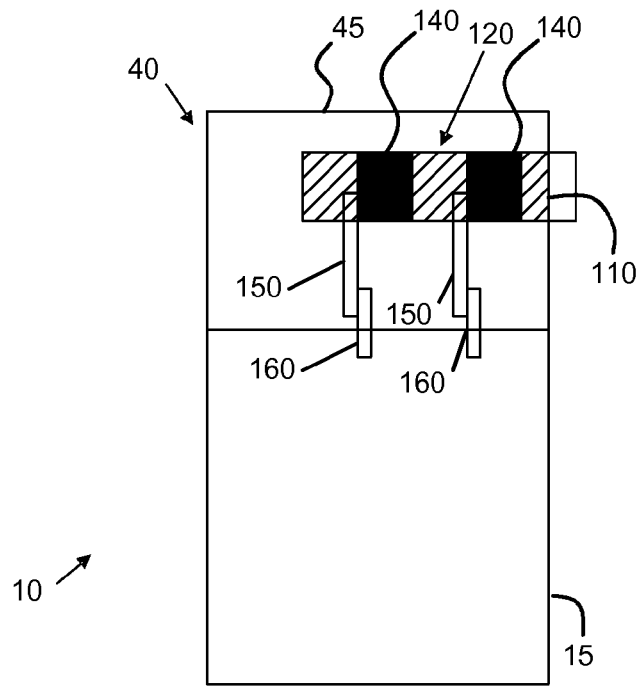

FIG. 5A shows a receptacle 120 having one conductive element 140, and FIG. 5B shows a receptacle 120 having two conductive elements 140. Of course, receptacle 120 may include any suitable number of conductive elements 140. It will be understood that connection header 40 may include any suitable number of lead receptacles 140, typically corresponding to the number of openings 110 defined by housing 45 of header 40.

Figure 6:
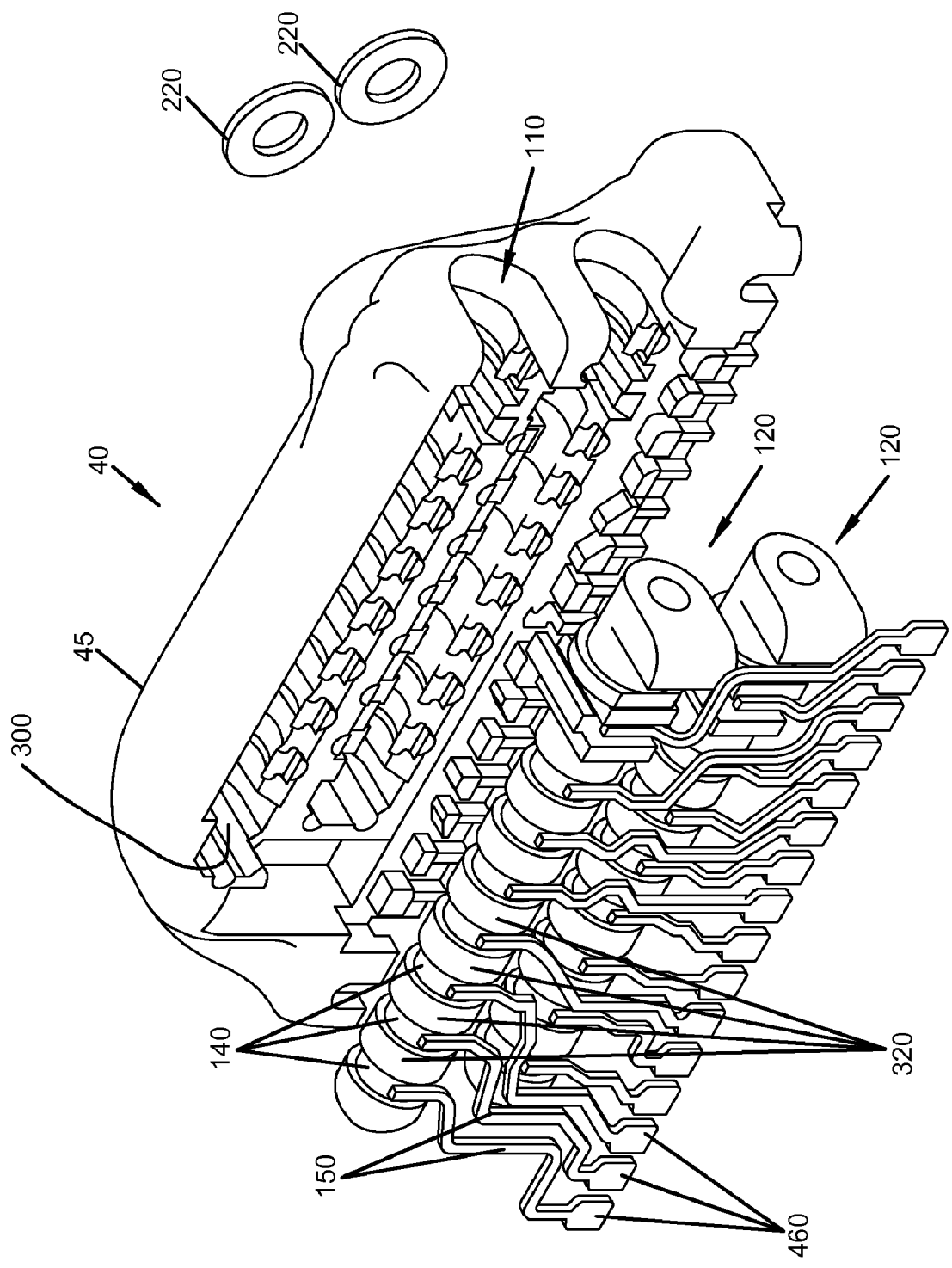
FIG. 6 is an exploded perspective view of portions of a representative connector header.

Referring to FIG. 6, an exploded perspective view of a representative connector header 40 is showing housing 45, lead receptacles 120 and securing elements 220. Portions of the interior surface of housing 45 defines recesses 300 configured to receive lead receptacles 120. Header housing 45 may be formed of any biocompatible material. In an embodiment, housing 45 is formed of a rigid plastic material (e.g., having a modulus of greater than 200 ksi), such as polysulfone. Additional information regarding connection headers having rigid plastic housings is provided in U.S. patent application Ser. No. 11/776,653, entitled "Connector Header for Implantable Medical Device", filed on even date herewith, and having which application is hereby incorporated herein by reference in its entirety to the extent that it does not conflict with the disclosure presented herein. Of course, housing 45 may be formed of less rigid material, such as polyurethane. While not shown, it will be understood that conventional methods for preparing connection headers may be employed. For example, receptacles may be placed in a rigid frame over which a housing may be molded.

Figure 7:
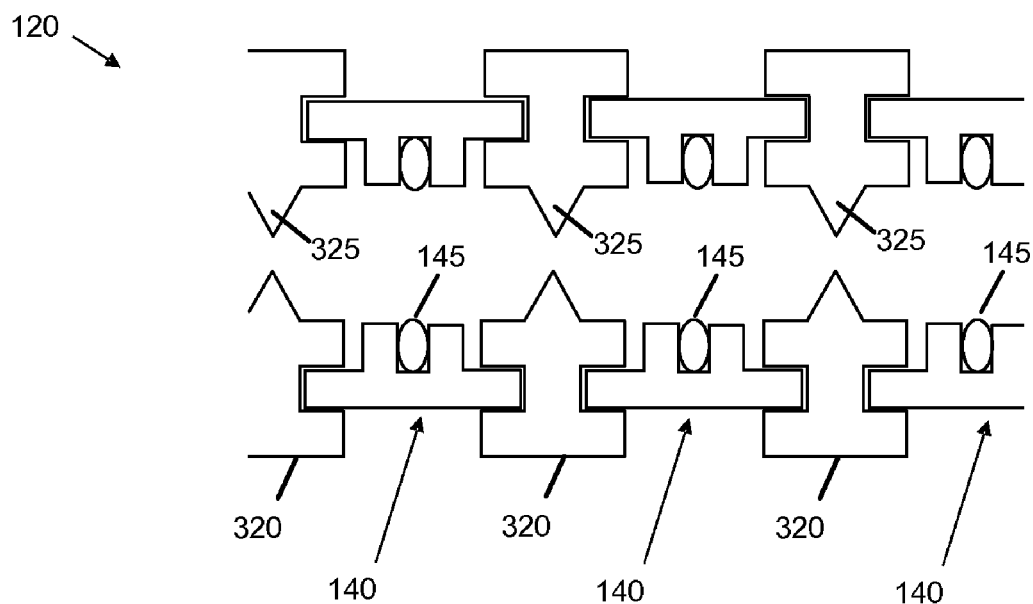
FIG. 7 is a schematic cross section of a representative lead receptacle.

FIG. 7 is a schematic cross section of a representative lead receptacle 120 showing conductive 140 and non-conductive 320 elements. Conductive elements 140 may be in the form of contact rings and may be formed of metallic material such as, for example, titanium, stainless steel, MP35N, niobium, tantalum, platinum, and alloys or combinations thereof. In many embodiments, the contact element includes an annular helical coil 145 (i.e., continuous coil spring 145) is disposed adjacent an inner surface of the electrically conducting contact ring 140. The helical annular coil 145 can be formed of any useful electrically conductive material such as, for example, a metal like gold, silver, titanium, platinum (e.g., platinum iridium) or the like. When a lead is inserted into the aperture of receptacle 120, the lead and lead contact(s) can deflect the annular helical coil 145 and form an electrical contact between the lead contact and the electrically conducting contact ring 140. The continuous coil spring 145 provides a frictional electrical and mechanical engagement (e.g., interference fit) with a lead contact and the adjacent electrically conducting contact ring 140. Non-conductive elements 320 provide electrical insulation between conductive elements 140 and may be formed of any suitable non-conductive, electrically insulating material, such as, for example, liquid silicone rubber, soft durometer polyurethane, and the like. In many embodiments, non-conductive elements 320 may include wiper sealing elements 325 that may deflect when a lead is inserted into receptacle 120 to prevent bodily fluid from entering the aperture of lead receptacle 120 when the device is implanted in a subject.

Receptacle 120 is typically assembled and held into place via longitudinally compressive force. A jacket, sleeve, or the like may be used to hold receptacle components in place.

Figure 8:
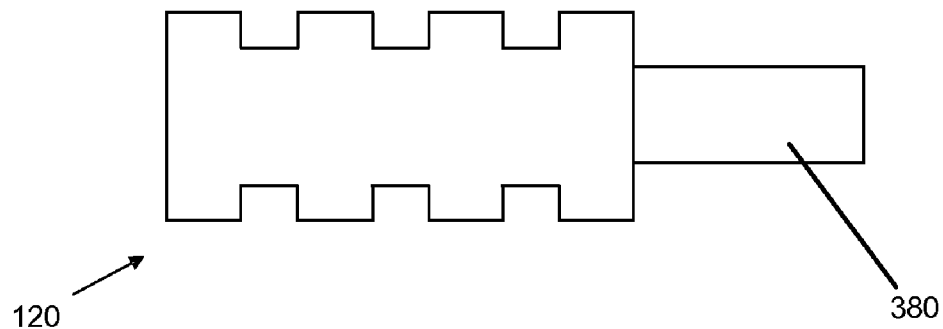
FIG. 8 is a side view of a lead receptacle disposed about and alignment pin.
Figure 9:
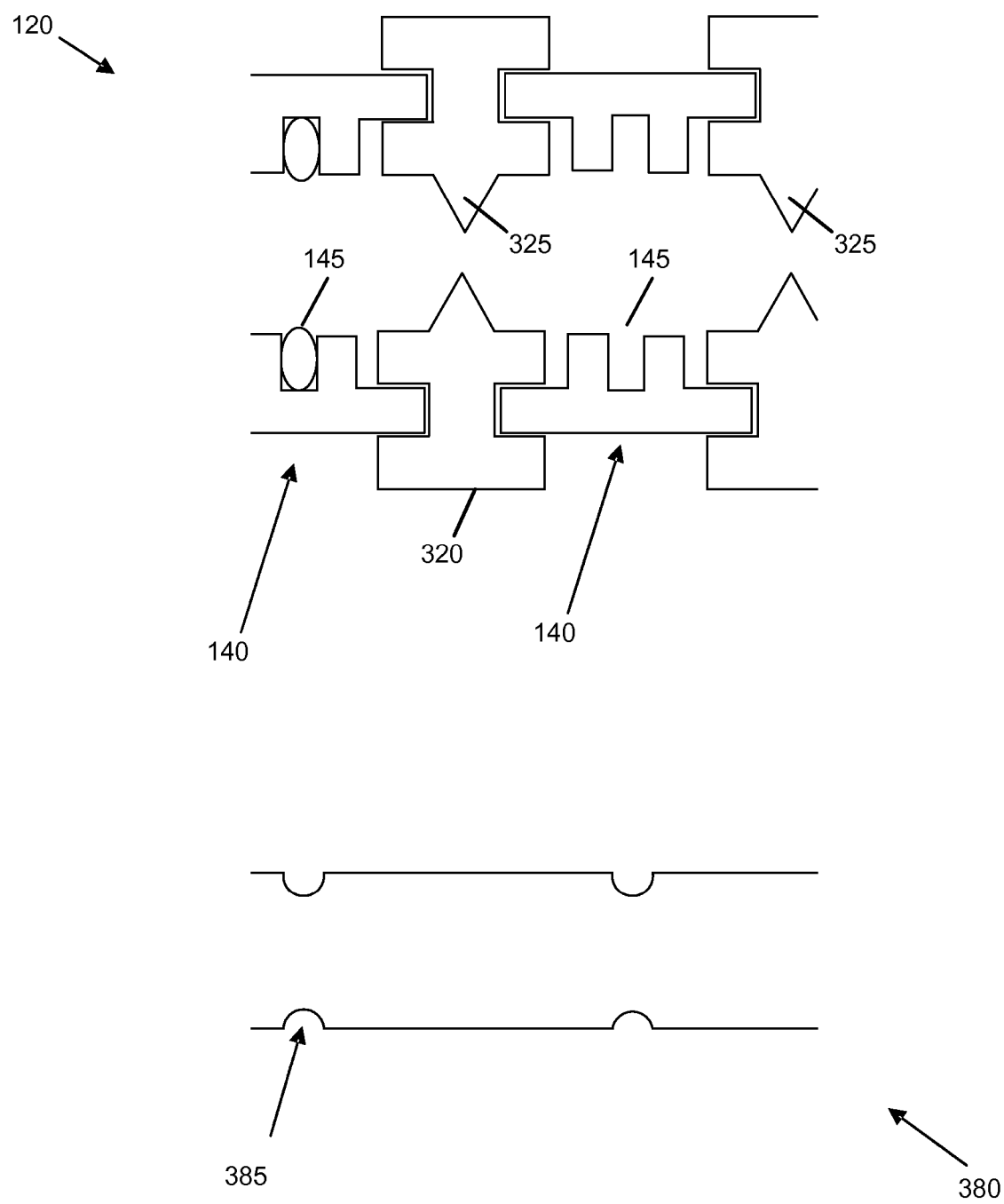
FIG. 9 is a schematic of an exploded cross-sectional view of a portion of lead receptacle and alignment pin.

Referring to FIG. 8, a side view of a lead receptacle 120 disposed about and alignment pin 380 or mandrel is shown. Lead receptacle 120 may be assembled on alignment pin 380 or placed about alignment pin 380 after being assembled. FIG. 9 shows a schematic of an exploded cross-sectional view of a portion of lead receptacle 120 and alignment pin 380. Alignment pin 380 may contain channels 385 or grooves for receiving annular helical coil 145 of conductive element 140 of receptacle 120 to facilitate proper alignment of components of receptacle 120 on alignment pin 380.

Figure 10:
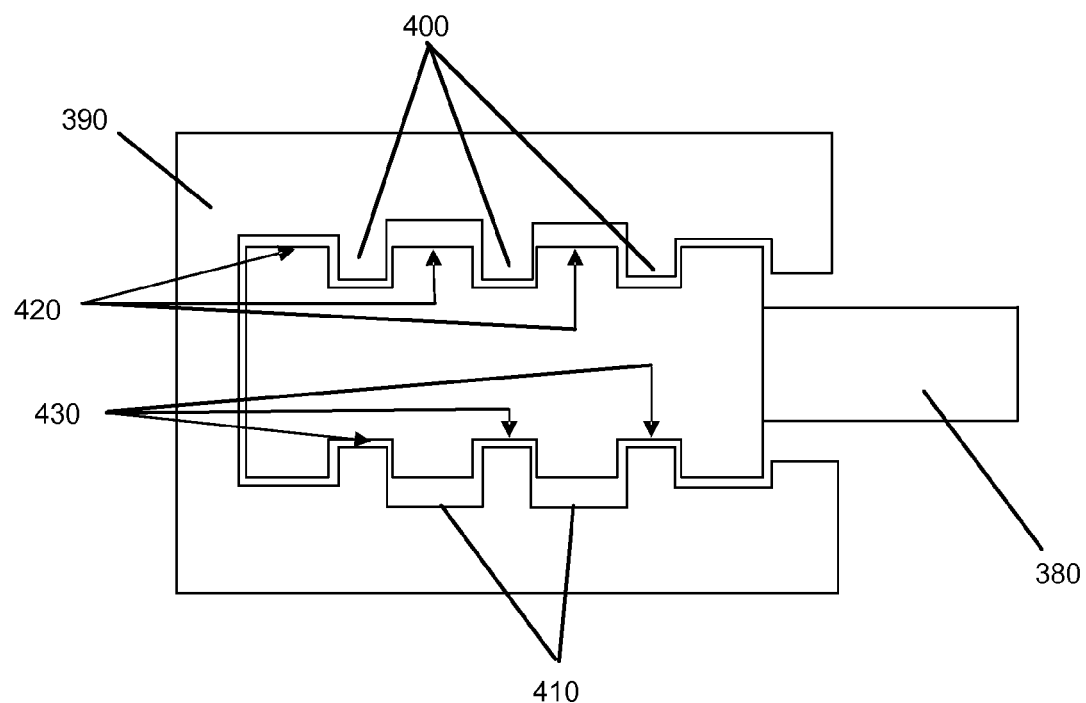
FIG. 10 is a side or top view of a lead receptacle disposed about alignment pin placed in a restraining fixture.

Lead receptacle 120 disposed about alignment pin 380 may be placed in a restraining fixture 390, as shown in the side or top view of FIG. 10. The restraining fixture 390 depicted in FIG. 10 has raised 400 and recessed 410 features complementary to raised 420 and recessed 430 portions of exterior surface of receptacle 120. In the embodiment depicted in FIG. 10, the raised exterior portions 420 of receptacle 120 correspond to non-conductive insulating portions 320, and the recessed portions 430 correspond to conductive portions 140. Restraining fixture 390 may include more than one recess if more than one lead receptacle 120 is to be used. Alternatively, multiple restraining fixtures 390 may be employed to accommodate more than one lead receptacle 120.

Figure 11:
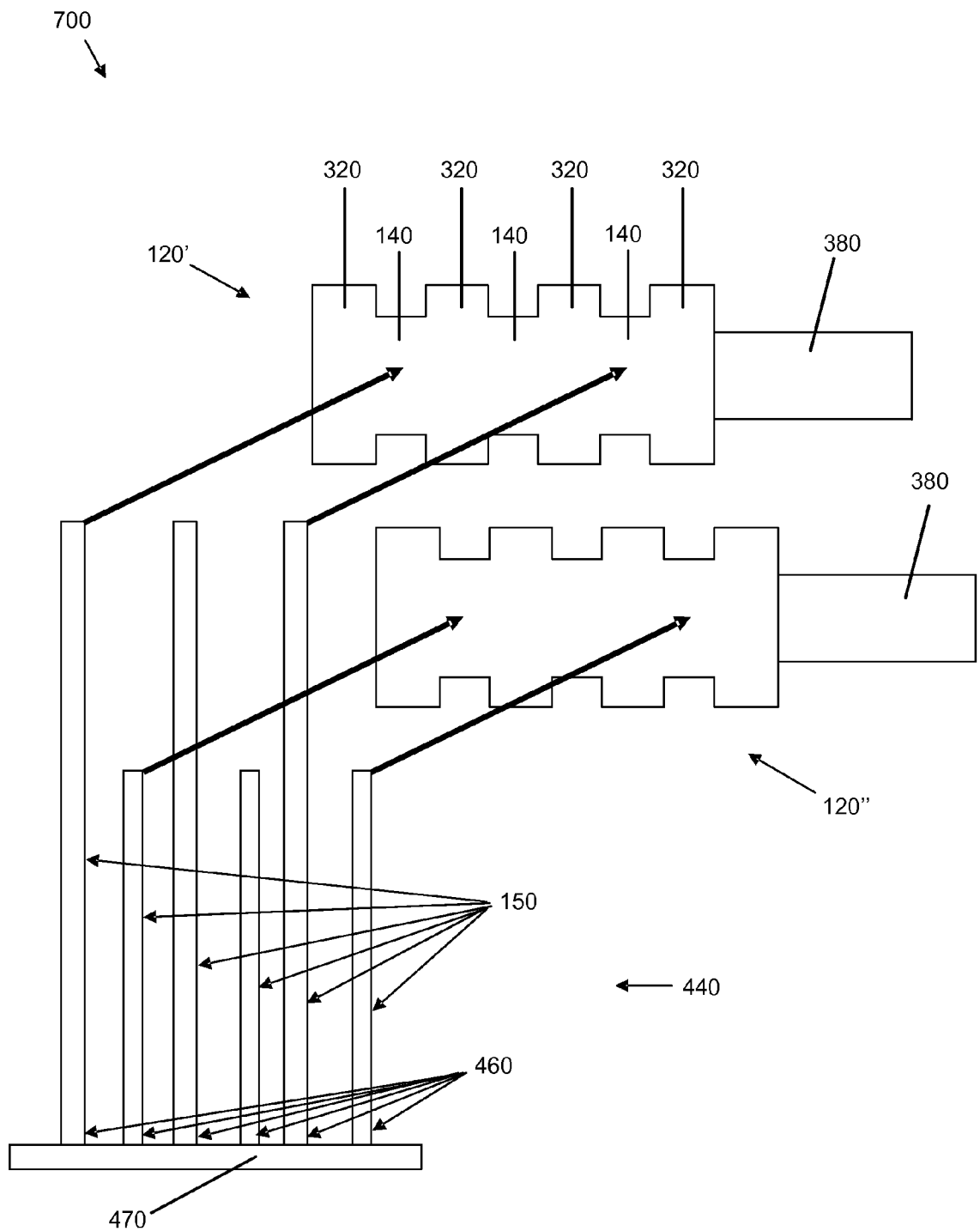
FIG. 11 is a perspective view of a representative lead receptacle and alignment pin and an exploded lead frame pin assembly.

FIG. 11 is a schematic view of a one-piece pin assembly 440 and lead receptacles 120 disposed about alignment pins 380. The pin assembly 440 includes a removable tab element 470 and conductors 150 having feedthrough coupling portions 460. In the embodiment depicted in FIG. 11, removable tab element 470 is attached to feedthrough coupling portions 460 of each of the conductors 150. However, it will be understood that tab element 470 may be connected, either directly or indirectly, to one or more conductors 150 configured to be attached to a first receptacle 120' and to one or more conductors 150 configured to be attached to a second receptacle 120" at any location along the conductors 150 where tab element 470 is capable of increasing the rigidity and dimensional stability of the overall receptacle/pin assembly 700 (i.e., the assembly where the one-piece pin assembly 440 is attached to a conductive portion of the first 120' and the second 120" receptacle). It will be further understood that pin assemblies 440 configured to be attached to more than two receptacles 120 are envisioned. Removable tab element 470 may be made of any material, but for ease of manufacture is preferably made of the same material as the conductive elements 150. Pin assembly 44 may be molded, stamped, or the like. A line of weakening may be the mechanism for removing tab element 470 from the rest of the pin assembly 440.

In various embodiments, tab element 470 is designed not to be removed. In such embodiments, tab element 470 is positioned such that it does not interfere with electrical coupling of feedthrough coupling portions 460 to feedthroughs of device and is preferably formed from non-conductive material, such as a rigid plastic material. Such tab elements 470 may be in any suitable form, such as a bar or the like molded about conductors 150.

Figure 12:
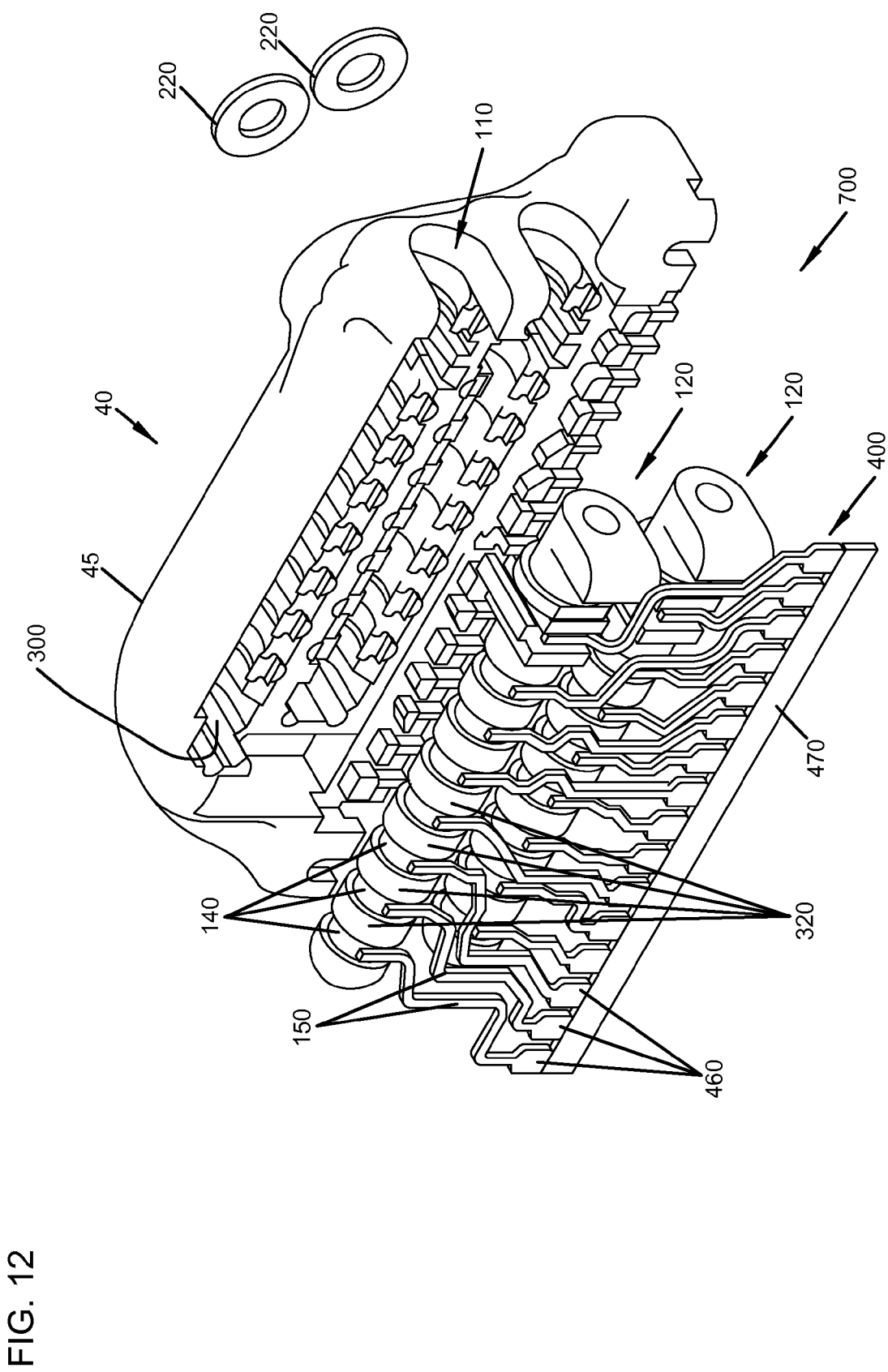
FIG. 12 is an exploded perspective view of portions of a representative connector header and one-piece receptacle/pin assembly.

Referring to FIG. 12, in which an exploded view of a connector header 40 is shown, a one-piece receptacle/pin assembly 700 including pin assembly 440 and lead receptacles 120 is inserted into header 40 such that receptacles 120 are inserted into recesses 300 defined by header housing 45. Removable tab element 470 serves to hold the first and second lead receptacles 120 in a somewhat rigid relative position until tab element 470 is removed. Due to the maintained spatial orientation, placement of receptacles 120 with attached lead frame pin assembly 440 into recesses 300 of connector block header housing 45 is facilitated. The structural rigidity and ease of placement of receptacles 120 with attached lead frame pin assembly 440 into recess 300 may be further facilitated by the presence of alignment pins 380 (not shown in FIG. 12).

Figure 13:
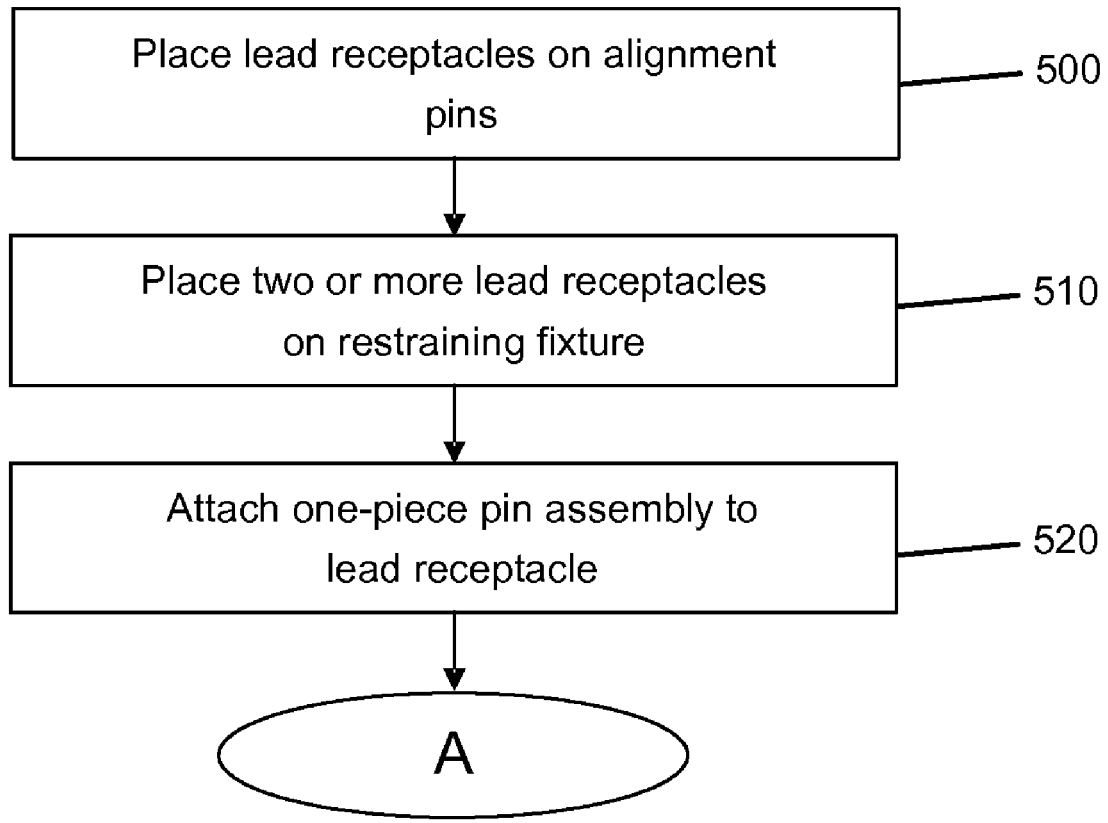
FIGS. 13-14 are flow diagrams or representative methods.
Figure 14:
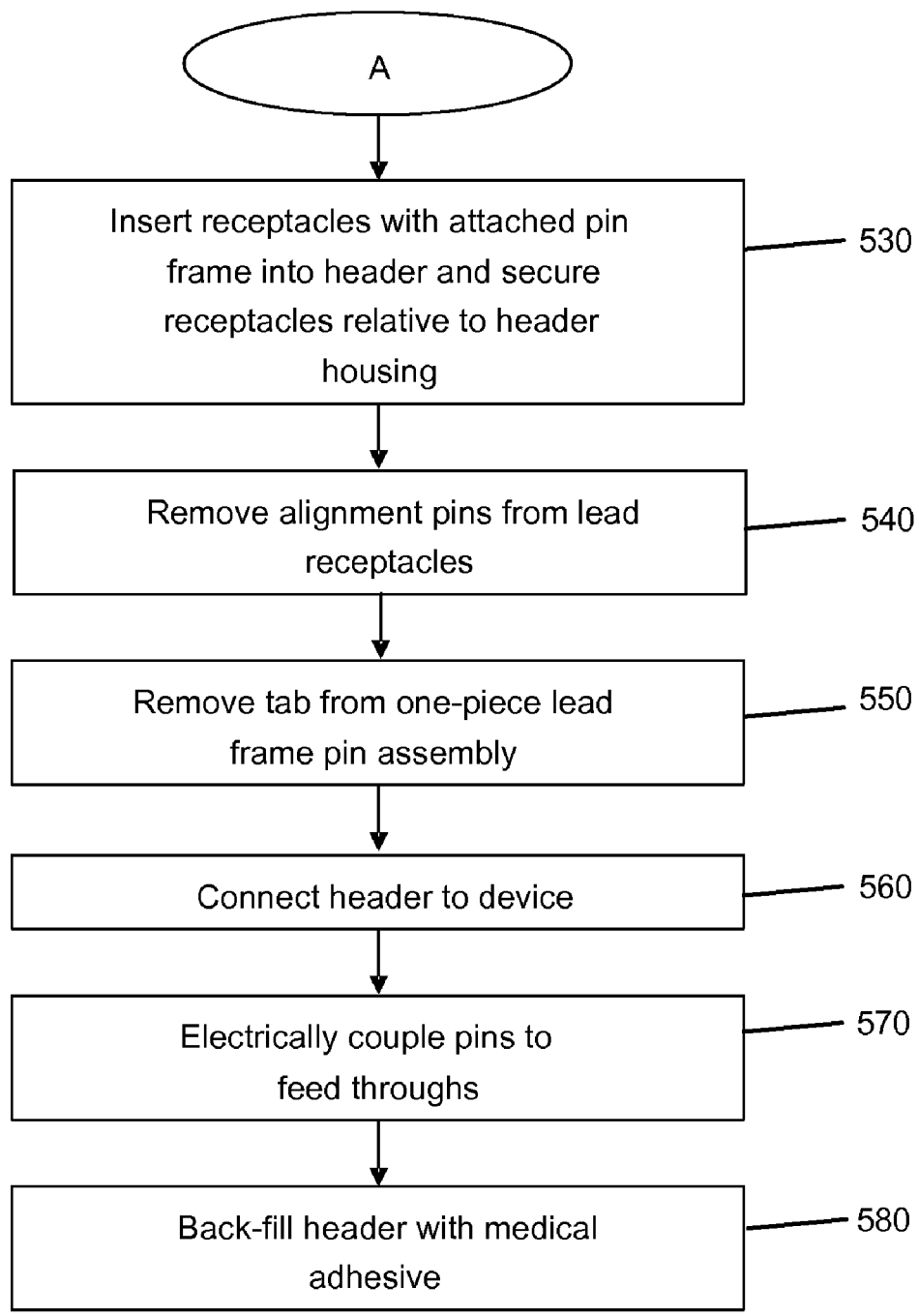

FIGS. 13-14 are a flow diagrams of illustrative methods. It will be understood that a method described with regard to FIGS. 13-14 or otherwise described in this disclosure may employ apparatuses, devices, and components other than those described herein. However, for the sake of convenience and clarity, the discussion that follows with regard to FIGS. 13-14 will be made with reference from time to time to the systems, devices, and components described with regard to FIGS. 1-12.

As shown in FIG. 13, lead receptacles 120 may be placed about alignment pins 380 (500) or may be assembled on alignment pins 380. Two or more lead receptacles 120 may be placed on one or more restraining fixtures 390 (510). Conductors 150 of a one-piece pin assembly 440 are attached and electrically coupled, e.g. by welding, to conductive portions 140 of lead receptacle 120 (520) while the receptacles 120 are received by restraining fixture 390 to produce a one-piece receptacle/pin assembly 700.

Referring to FIG. 14, the receptacle/pin assembly 700 may be inserted into a header 40 and securing receptacles relative to header housing 45 (530). The assembly 700 may be inserted into header 40 such that receptacles 120 are inserted into recesses 300 of header housing 45 or may be accomplished by inserting receptacles into a frame to be overmolded with polymeric material to form header housing. If the receptacles 120 are inserted into recesses 300 of header housing 45, receptacles 120 are secured relative to housing via mechanical attachment, adhesive, overmolding or the like. The alignment pins 380 may be removed from the receptacles 120 (540) before or after the receptacles 120 are secured relative to the header housing 45. However, it may be desirable to remove alignment pins 380 after receptacles 120 are secured relative to header housing 45 to facilitate maintaining proper receptacle 120 alignment.

The removable tab element(s) 470 may be removed (550), the header 40 may be connected to an appropriate device 10 (560), and feedthrough coupling portions 460 of conductors 150 may be electrically coupled to feedthroughs 160 of device 10. If appropriate, header 40 may be completed by backfilling header housing 45 with appropriate polymer, such as medical adhesive, or by overmolding header housing 45. Medical adhesive or other suitable biocompatible polymer, such as liquid silicone rubber, may be used to fill voids between pin assembly 440, header housing 45, and receptacles 120 and to electrically insulate receptacles 120, conductors 150 and feedthroughs 160.

One of skill in the art will understand that components or steps described herein regarding a given embodiment or set of embodiments may readily be omitted, substituted, or added from, with, or to components or steps of other embodiments or sets of embodiments, as appropriate or desirable.

Thus, embodiments of LEAD RECEPTACLE AND PIN FRAME ASSEMBLY are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
   placing about a first alignment pin a first lead receptacle having a conductive portion;
   placing about a second alignment pin a second lead receptacle having a conductive portion;
   placing the first and second lead receptacles on a restraining fixture;
   attaching and electrically coupling a first conductor of a one-piece lead frame pin assembly to the conductive portion of the first receptacle,
      wherein the lead frame pin assembly has a tab element connecting a first conductor to a second conductor, the first conductor including a feedthrough coupling portion, and the second conductor including a feedthrough coupling portion; and
   attaching and electrically coupling the second conductor of the lead frame assembly to the conductive portion of the second receptacle.

2. The method of claim 1, wherein placing the first lead receptacle about the first alignment pin comprises assembling components of the first receptacle on the first alignment pin, and wherein placing the second lead receptacle about the second alignment pin comprises assembling components of the second receptacle on the second alignment pin.

3. The method of claim 1, wherein attaching and electrically coupling the first conductor to the conductive portion of the first receptacle comprises welding the first conductor to the conductive portion of the first receptacle, and wherein attaching and electrically coupling the second conductor to the conductive portion of the second receptacle comprises welding the second conductor to the conductive portion of the second receptacle.

4. The method of claim 1, further comprising:
   inserting the first and second lead receptacles with attached lead frame pin assembly into a connector block header housing such that the first and second receptacles are received by first and second recesses of the header housing; and
   securing the first and second lead receptacles to the header housing.

5. The method of claim 4, further comprising:
   removing the tab element.

6. The method of claim 5, further comprising:
   electrically coupling feedthrough coupling portion of the first conductor to a first and feedthrough of an implantable medical device, and electrically coupling the feedthrough coupling portion of the second conductor to a second feedthrough of the implantable medical device.

7. The method of claim 6, further comprising:
   attaching the header housing to the device housing.

8. The method of claim 7, further comprising:
   removing the first and second alignment pins from the first and second lead receptacles.

9. A lead receptacle and pin assembly comprising:
   first and second lead receptacles, each having a conductive portion; and
   a one-piece lead frame pin assembly attached to the conductive portions of the first and second lead receptacles,
   wherein the one-piece lead frame pin assembly comprises first and second conductors connected via a tab element, the first conductor having (i) a receptacle coupling portion that is attached and electrically coupled to the conductive portion of the first lead receptacle and (ii) a feedthrough coupling portion configured to be electrically coupled to a first feedthrough of an implantable medical device,
      the second conductor having (i) a receptacle coupling portion that is attached and electrically coupled to the conductive portion of the first lead receptacle and (ii) a feedthrough coupling portion configured to be electrically coupled to a second feedthrough of the implantable medical device.

10. The lead receptacle and pin assembly of claim 9, wherein the tab element is removably attached to the feedthrough coupling portions of the first and second conductors.

11. The lead receptacle and pin assembly of claim 10, wherein the pin assembly comprises more than two conductors, each having a feedthrough coupling portion, and wherein the tab element is removably attached to each of the feedtrhough coupling portions.

12. The lead receptacle and pin assembly of claim 9, wherein the tab element is removable along a line of weakening.

13. The lead receptacle and pin assembly of claim 9, wherein the pin assembly is substantially planar.

14. A connector header assembly comprising:
a housing defining first and second recesses; and
the lead receptacle and pin assembly of claim 9,
wherein the first receptacle is disposed in the first recess and the second receptacle is disposed in the second recess.

15. The connector header assembly of claim 14, wherein the header housing is formed of a plastic material having a modulus of greater than 200 ksi.

16. The connector header assembly of claim 9, wherein the header housing is formed of polysulfone.

* * * * *